(12) United States Patent
Aoyama et al.

(10) Patent No.: US 12,423,819 B2
(45) Date of Patent: Sep. 23, 2025

(54) MEDICAL IMAGE PROCESSING APPARATUS, MEDICAL IMAGE PROCESSING METHOD, AND STORAGE MEDIUM

(71) Applicants: The University of Tokyo, Tokyo (JP); CANON MEDICAL SYSTEMS CORPORATION, Tochigi (JP)

(72) Inventors: Gakuto Aoyama, Nasushiobara (JP); Ichiro Sakuma, Bunkyo-ku (JP); Minoru Ono, Bunkyo-ku (JP); Shu Takagi, Bunkyo-ku (JP); Asuka Hatano, Bunkyo-ku (JP); Haruo Yamauchi, Bunkyo-ku (JP); Eriko Maeda; Naoki Tomii, Bunkyo-ku (JP); Hiroyuki Tsukihara, Bunkyo-ku (JP)

(73) Assignees: The University of Tokyo, Tokyo (JP); CANON MEDICAL SYSTEMS CORPORATION, Tochigi (JP)

(*) Notice: Subject to any disclaimer, the term of this patent is extended or adjusted under 35 U.S.C. 154(b) by 368 days.

(21) Appl. No.: 17/947,553

(22) Filed: Sep. 19, 2022

(65) Prior Publication Data
US 2023/0086533 A1    Mar. 23, 2023

(30) Foreign Application Priority Data
Sep. 21, 2021    (JP) ............................ 2021-153068

(51) Int. Cl.
G06T 7/00    (2017.01)
A61B 6/00    (2024.01)
A61B 6/50    (2024.01)

(52) U.S. Cl.
CPC ............ *G06T 7/0016* (2013.01); *A61B 6/507* (2013.01); *A61B 6/5217* (2013.01); *G06T 2207/30104* (2013.01)

(58) Field of Classification Search
USPC ........................................................ 382/128
See application file for complete search history.

(56) References Cited

U.S. PATENT DOCUMENTS 10,945,678 B2    3/2021    Oka et al.
2018/0344262 A1    12/2018    Oka et al.
(Continued)

FOREIGN PATENT DOCUMENTS

| JP | 2008-513067 A | 5/2008 |
| JP | 2018-202147 A | 12/2018 |
| JP | 2020-058647 A | 4/2020 |

OTHER PUBLICATIONS

Office Action issued Jun. 4, 2025, in corresponding Japanese Patent Application No. 2021-153068, 3 pages.

*Primary Examiner* — Darryl V Dottin
(74) *Attorney, Agent, or Firm* — Oblon, McClelland, Maier &Neustadt, L.L.P.

(57) ABSTRACT

A medical image processing apparatus according to an embodiment includes processing circuitry. The processing circuitry is configured to obtain a medical image. The processing circuitry is configured to calculate a first blood flow direction on the basis of a structure of a region of interest rendered in the medical image. The processing circuitry is configured to calculate a second blood flow direction on the basis of a structure in the surroundings of the region of interest. The processing circuitry is configured to identify a condition of the region of interest, on the basis of the first blood flow direction and the second blood flow direction.

14 Claims, 11 Drawing Sheets

(56) References Cited

U.S. PATENT DOCUMENTS

2020/0311917 A1* 10/2020 Segawa ................ A61B 5/0261
2020/0372634 A1* 11/2020 Chiribiri ............... G06T 7/0012

* cited by examiner

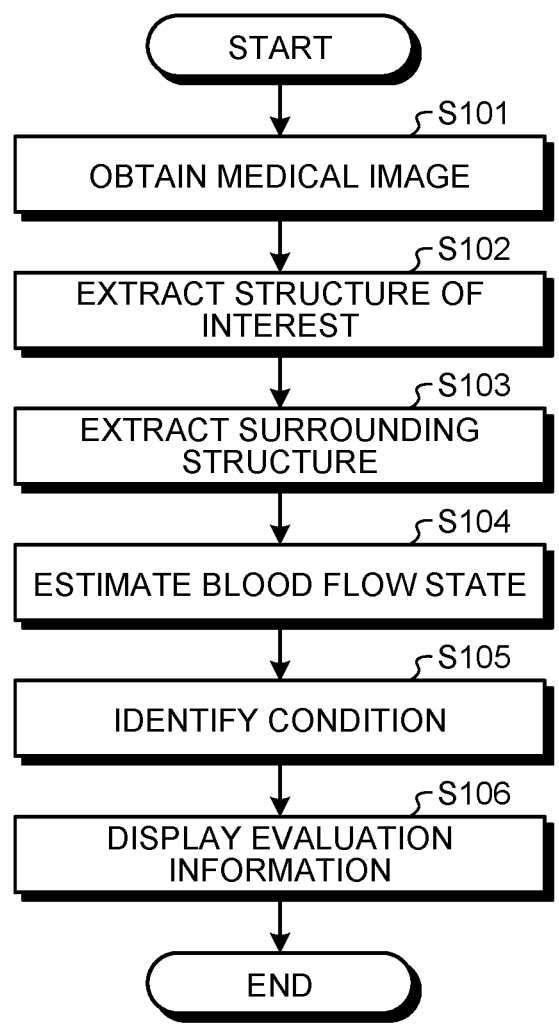

FIG.6

| DISEASE RISK | ANGLE | WARNING PHRASES |
|---|---|---|
| HIGH | 45° TO 90° | CHECK FOR PRESENCE OF AORTIC DISEASE. IF NO ABNORMALITY IS FOUND, CONSIDER GIVING DIFFERENT EXAMINATION. |
| MEDIUM | 21° TO 44° | CHECK FOR PRESENCE OF AORTIC DISEASE |
| LOW | 0° TO 20° | - |
| ERROR | 90° OR LARGER | UNABLE TO CALCULATE AORTIC DISEASE RISK. VISUAL CHECKING IS RECOMMENDED. |

FIG.7A
BLOOD FLOW CIRCULATION RISK OF PATIENT IS MEDIUM. CHECK FOR PRESENCE OF AORTIC VALVE DISEASE.
FIG.7B
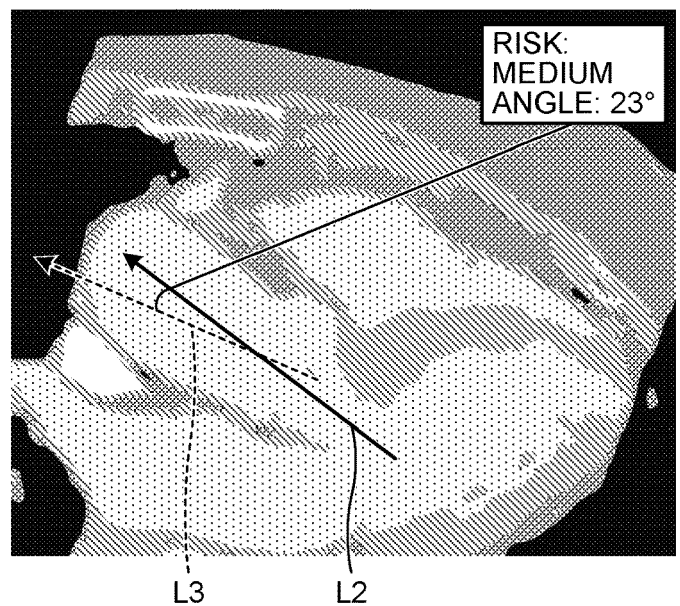
FIG.7C
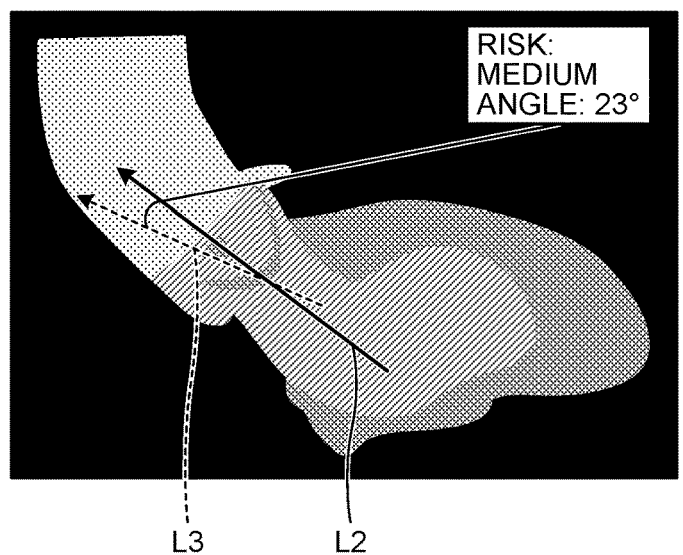

MEDICAL IMAGE PROCESSING APPARATUS, MEDICAL IMAGE PROCESSING METHOD, AND STORAGE MEDIUM

CROSS-REFERENCE TO RELATED APPLICATIONS

This application is based upon and claims the benefit of priority from Japanese Patent Application No. 2021-153068, filed on Sep. 21, 2021; the entire contents of which are incorporated herein by reference.

FIELD

Embodiments described herein relate generally to a medical image processing apparatus, a medical image processing method, and a storage medium.

BACKGROUND

Conventionally, a technique is known by which the shapes of anatomical structures of a human body are extracted from a medical image. Further, another technique is also known by which, on the basis of characteristics of the shapes of anatomical structures extracted by using the abovementioned technique, a diagnosed name of a disease or the degree of an abnormality related to the anatomical structures is estimated and evaluated.

BRIEF DESCRIPTION OF THE DRAWINGS

FIG. 2 is a flowchart illustrating a processing procedure of processes performed by processing functions included processing circuitry of the medical image processing apparatus according to the first embodiment;

FIG. 6 is a drawing illustrating an example of correspondence information according to the first embodiment;

FIG. 7A is a drawing illustrating an example of evaluation information according to the first embodiment;

FIG. 7B is a drawing illustrating another example of the evaluation information according to the first embodiment;

FIG. 7C is a drawing illustrating yet another example of the evaluation information according to the first embodiment;

DETAILED DESCRIPTION

Figure 1:
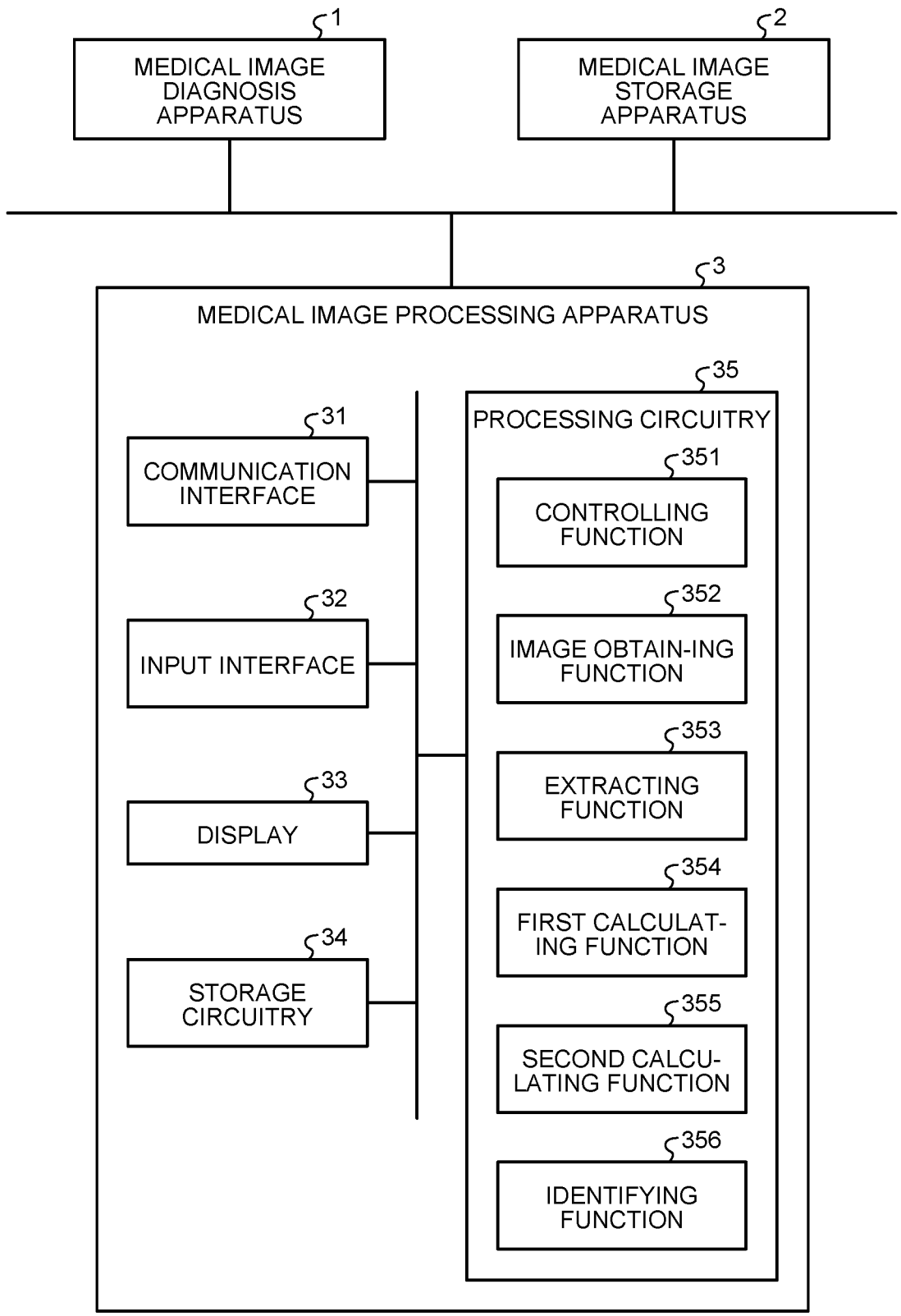
FIG. 1 is a diagram illustrating an exemplary configuration of a medical image processing apparatus according to a first embodiment.

A medical image processing apparatus according to an embodiment includes processing circuitry. The processing circuitry is configured to obtain a medical image. The processing circuitry is configured to calculate a first blood flow direction on the basis of a structure of a region of interest rendered in the medical image. The processing circuitry is configured to calculate a second blood flow direction on the basis of a structure in the surroundings of the region of interest. The processing circuitry is configured to identify a condition of the region of interest, on the basis of the first blood flow direction and the second blood flow direction.

In the following sections, exemplary embodiments of a medical image processing apparatus, a medical image processing method, and a storage medium will be explained in detail, with reference to the accompanying drawings. Possible embodiments of the medical image processing apparatus, the medical image processing method, and the storage medium of the present disclosure are not limited to the embodiments described below. Further, in the following sections, some of the constituent elements that are the same as each other will be referred to by using the same reference characters, and duplicate explanations thereof will be omitted.

First Embodiment

FIG. 1 is a diagram illustrating an exemplary configuration of a medical image processing apparatus according to a first embodiment. For example, as illustrated in FIG. 1, a medical image processing apparatus 3 according to the present embodiment is communicably connected to a medical image diagnosis apparatus 1 and a medical image storage apparatus 2 via a network. Further, other various types of apparatuses and systems may be connected to the network illustrated in FIG. 1.

The medical image diagnosis apparatus 1 is configured to image an examined subject (hereinafter, "subject") and to generate medical images. Further, the medical image diagnosis apparatus 1 is configured to transmit the generated medical images to any of the various types of apparatuses in the network. For example, the medical image diagnosis apparatus 1 may be an X-ray diagnosis apparatus, an X-ray Computed Tomography (CT) apparatus, a Magnetic Resonance Imaging (MRI) apparatus, an ultrasound diagnosis apparatus, a Single Photon Emission Computed Tomography (SPECT) apparatus, a Positron Emission computed Tomography (PET) apparatus, or the like.

The medical image storage apparatus 2 is configured to store therein various types of medical images related to the subject. More specifically, the medical image storage apparatus 2 is configured to receive the medical images from the medical image diagnosis apparatus 1 via the network and to store and save the medical images in storage circuitry provided therein. For example, the medical image storage apparatus 2 is realized by using a computer device such as a server or a workstation. Further, for example, the medical image storage apparatus 2 may be realized as a Picture Archiving and Communication System (PACS) or the like, so as to store therein the medical images in a format compliant with Digital Imaging and Communications in Medicine (DICOM).

The medical image processing apparatus 3 is configured to perform various types of information processing processes related to the subject. More specifically, the medical image processing apparatus 3 is configured to receive the medical images from the medical image diagnosis apparatus 1 or the medical image storage apparatus 2 via the network and to perform the various types of information processing processes while using the medical images. For example, the medical image processing apparatus 3 is realized by using a computer device such as a server or a workstation.

For example, the medical image processing apparatus 3 includes a communication interface 31, an input interface 32, a display 33, storage circuitry 34, and processing circuitry 35.

The communication interface 31 is configured to control communication and transfer of various types of data transmitted and received between the medical image processing apparatus 3 and any of the other apparatuses connected via the network. More specifically, the communication interface 31 is connected to the processing circuitry 35 and is configured to transmit data received from another apparatus to the processing circuitry 35 and to transmit data transmitted thereto from the processing circuitry 35 to one or more other apparatuses. For example, the communication interface 31 is realized by using a network card, a network adaptor, a Network Interface controller (NIC), or the like.

The input interface 32 is configured to receive, from a user, operations to input various types of instructions and various types of information. More specifically, the input interface 32 is connected to the processing circuitry 35 and is configured to convert the input operations received from the user into electrical signals and to transmit the electrical signals to the processing circuitry 35. For example, the input interface 32 is realized by using a trackball, a switch button, a mouse, a keyboard, a touchpad on which input operations can be performed by touching an operation surface thereof, a touch screen in which a display screen and a touchpad are integrally formed, a contactless input interface using an optical sensor, an audio input interface, and/or the like. In the present disclosure, the input interface 32 does not necessarily have to include physical operation component parts such as a mouse, a keyboard, and/or the like. For instance, possible examples of the input interface 32 include an electrical signal processing circuit configured to receive an electrical signal corresponding to an input operation from an external input device provided separately from the apparatus and to transmit the electrical signal to a controlling circuit.

The display 33 is configured to display various types of information and various types of data. More specifically, the display 33 is connected to the processing circuitry 35 and is configured to display various types of information and various types of data received from the processing circuitry 35. For example, the display 33 is realized by using a liquid crystal display, a Cathode Ray Tube (CRT) display, a touch panel, or the like.

The storage circuitry 34 is configured to store therein various types of data and various types of programs. More specifically, the storage circuitry 34 is connected to the processing circuitry 35 and is configured to store therein data received from the processing circuitry 35 and to read and transmit any of the data stored therein to the processing circuitry 35. For example, the storage circuitry 34 is configured by using a semiconductor memory element such as a Random Access Memory (RAM) or a flash memory, a hard disk, an optical disk, or the like.

The processing circuitry 35 is configured to control the entirety of the medical image processing apparatus 3. For example, the processing circuitry 35 is configured to perform various types of processes in accordance with the input operations received from the user via the input interface 32. For example, the processing circuitry 35 is configured to receive data transmitted from another apparatus via the communication interface 31 and to store the received data into the storage circuitry 34. Further, for example, by transmitting any of the received data from the storage circuitry 34 to the communication interface 31, the processing circuitry 35 is configured to transmit the data to another apparatus. In addition, for example, the processing circuitry 35 is configured to cause the display 33 to display any of the data received from the storage circuitry 34.

The exemplary configuration of the medical image processing apparatus 3 according to the present embodiment has thus been explained. For example, the medical image processing apparatus 3 according to the present embodiment is installed in a medical facility such as a hospital or a clinic and is configured to assist various types of diagnosing processes and treatment planning performed by the user such as a medical doctor. For example, the medical image processing apparatus 3 is configured to perform various types of processes for appropriately estimating a condition of a region of interest.

As explained above, the technique is known by which, on the basis of the shape of a region of interest extracted from a medical image, a diagnosis name or the degree of an abnormality is estimated. However, even when organs (e.g., valves) have mutually the same shape or bring out mutually the same blood flow state, the degree of an abnormality or a prognostic risk caused by the shape or the blood flow state of the region of interest may vary, depending on a relationship with the shape of an organ positioned in the surroundings of the organ. As a result, according to the existing estimation technique based on the shape of a region of interest, it may be impossible in some situations to appropriately estimate the degree of an abnormality or a prognostic risk caused by the shape or a blood flow state of the organ of interest.

To cope with this situation, the medical image processing apparatus 3 according to the present embodiment is configured to be able to appropriately estimate a condition of a region of interest, by identifying the condition of the region of interest on the basis of the structure of the region of interest and the structure of a region in the surroundings of the region of interest. More specifically, on the basis of the structure of the region of interest, the medical image processing apparatus 3 is configured to calculate a first blood flow direction in the region of interest, to further calculate a second blood flow direction in a surrounding structure on the basis of the surrounding structure, so as to identify the condition of the region of interest on the basis of the first blood flow direction and the second blood flow direction. Next, the medical image processing apparatus 3 configured as described above will be explained in detail.

For example, as illustrated in FIG. 1, in the present embodiment, the processing circuitry 35 of the medical image processing apparatus 3 is configured to implement a controlling function 351, an image obtaining function 352, an extracting function 353, a first calculating function 354, a second calculating function 355, and an identifying function 356. In this situation, the processing circuitry 35 is an example of processing circuitry.

The controlling function 351 is configured to generate various types of Graphical User Interfaces (GUIs) and various types of display information in accordance with operations received via the input interface 32 and to control the display 33 to display the GUIs and the display information. For example, the controlling function 351 is configured to cause the display 33 to display a GUI used for setting the region of interest and a surrounding region and evaluation information that evaluates the condition of the region of interest identified on the basis of the blood flow directions. Further, the controlling function 351 is also capable of generating various types of display images on the basis of a medical image obtained by the image obtaining function 352.

The image obtaining function 352 is configured to obtain a medical image of the subject from the medical image diagnosis apparatus 1 or the medical image storage apparatus 2 via the communication interface 31. More specifically, the image obtaining function 352 is configured to obtain the medical image including morphological information about three-dimensional anatomical structures of the region of interest and the surrounding region thereof to be processed. In an example, the image obtaining function 352 may be configured to obtain a plurality of medical images obtained by three-dimensionally performing an image taking process multiple times in a time direction. For example, as the plurality of images, the image obtaining function 352 is configured to obtain CT images, ultrasound images, MRI images, X-ray images, angiography images, PET images, SPECT images, or the like. By implementing the image obtaining function 352, the processing circuitry 35 is configured to receive at least one medical image of the subject from the medical image diagnosis apparatus 1 or the medical image storage apparatus 2 and to store the received medical image into the storage circuitry 34.

With respect to the medical image obtained by the image obtaining function 352, the extracting function 353 is configured to extract the structure of the region of interest (hereinafter, "structure of interest") and the structure of the region in the surroundings of the region of interest (hereinafter, "surrounding structure"). More specifically, the extracting function 353 is configured to extract the structure of interest and the surrounding structure of which the conditions are to be evaluated. For example, the extracting function 353 is configured to extract a heart valve as the structure of interest and a blood vessel connected to the heart valve or the like as the surrounding structure. Processes performed by the extracting function 353 will be explained in detail later.

With respect to the medical image obtained by the image obtaining function 352, the first calculating function 354 is configured to calculate the first blood flow direction in the region of interest. For example, the first calculating function 354 is configured to calculate a blood flow direction caused by the heart valve extracted as the structure of interest. Processes performed by the first calculating function 354 will be explained in detail later.

With respect to the medical image obtained by the image obtaining function 352, the second calculating function 355 is configured to calculate the second blood flow direction in the region in the surroundings of the region of interest. For example, the second calculating function 355 is configured to calculate the blood flow direction caused by the blood vessel or the like extracted as the surrounding structure. Processes performed by the second calculating function 355 will be explained in detail later.

The identifying function 356 is configured to identify the condition of the region of interest on the basis of the first blood flow direction and the second blood flow direction. For example, the identifying function 356 is configured to identify a condition of the heart valve, on the basis of the blood flow direction caused by the structure of the heart valve and the blood flow direction caused by the structure of the blood vessel connected to the heart valve. In other words, the identifying function 356 is configured to identify the condition caused in the human body by the region of interest (e.g., the heart valve). Processes performed by the identifying function 356 will be explained in detail later.

For example, the abovementioned processing circuitry 35 is realized by using a processor. In that situation, the processing functions described above are stored in the storage circuitry 34 in the form of computer-executable programs. Further, the processing circuitry 35 is configured to realize the functions corresponding to the programs, by reading and executing the programs stored in the storage circuitry 34. In other words, the processing circuitry 35 that has read the programs has the processing functions illustrated in FIG. 1.

Further, it is also acceptable to structure the processing circuitry 35 by combining together a plurality of independent processors, so that the processing functions are realized as a result of the processors executing the programs. Further, the processing functions included in the processing circuitry 35 may be realized as being distributed among or integrated together in one or more processing circuits, as appropriate. Furthermore, the processing functions included in the processing circuitry 35 may be realized by using a combination of hardware such as circuitry and software. In addition, although the example was explained above in which the programs corresponding to the processing functions are stored in the single storage circuit (i.e., the storage circuitry 34), possible embodiments are not limited to this example. For instance, it is also acceptable to store the programs corresponding to the processing functions in a plurality of storage circuits in a distributed manner, so that the processing circuitry 35 reads and executes the programs from the storage circuits.

Next, a procedure of processes performed by the medical image processing apparatus 3 will be explained with reference to FIG. 2, before explaining details of the processes. FIG. 2 is a flowchart illustrating the processing procedure of the processes performed by the processing functions included the processing circuitry 35 of the medical image processing apparatus 3 according to the first embodiment.

For example, as illustrated in FIG. 2, in the present embodiment, the image obtaining function 352 obtains at least one medical image of the subject from the medical image diagnosis apparatus 1 or the medical image storage apparatus 2 (step S101). For example, in response to a medical image obtaining operation received via the input interface 32, the image obtaining function 352 obtains a plurality of medical images which include morphological information about anatomical structures of a biological organ to be processed and in which the biological organ is in mutually-different conditions. This process is realized, for example, as a result of the processing circuitry 35 invoking and executing a program corresponding to the image obtaining function 352 from the storage circuitry 34.

Subsequently, with respect to the obtained medical images, the extracting function 353 extracts the structure of interest included in the medical images (step S102) and extracts the surrounding structure (step S103). This process is realized, for example, as a result of the processing circuitry 35 invoking and executing a program corresponding to the extracting function 353 from the storage circuitry 34. Although FIG. 2 illustrates the processing procedure in which the structure of interest is extracted, and subsequently, the surrounding structure is extracted, possible embodiments are not limited to this example. It is also acceptable to extract the surrounding structure before extracting the structure of interest. It is also acceptable to extract the structure of interest and the surrounding structure at the same time.

After that, the first calculating function 354 and the second calculating function 355 estimate a blood flow state (step S104). More specifically, the first calculating function 354 calculates a blood flow direction (the first blood flow direction) caused by the structure of interest, whereas the second calculating function 355 calculates a blood flow direction (the second blood flow direction) caused by the surrounding structure. This process is realized, for example, as a result of the processing circuitry 35 invoking and executing programs corresponding to the first calculating function 354 and the second calculating function 355 from the storage circuitry 34.

Subsequently, the identifying function 356 identifies the condition of the structure of interest on the basis of a first blood flow state and a second blood flow state (step S105). This process is realized, for example, as a result of the processing circuitry 35 invoking and executing a program corresponding to the identifying function 356 from the storage circuitry 34.

After that, the controlling function 351 causes the display 33 to display the evaluation information based on the identified condition (step S106). This process is realized, for example, as a result of the processing circuitry 35 invoking and executing a program corresponding to the controlling function 351 from the storage circuitry 34.

Next, details of the processes performed by the medical image processing apparatus 3 will be explained. In the following sections, an example will be explained in which the aortic valve is used as the structure of interest, whereas the ascending aorta into which blood flows via the aortic valve is used as the surrounding structure. However, possible sites to be processed by the processes described in the present embodiment are not limited to these examples. It is possible to perform the processes on any biological organ in the human body as long as fluid or gas is involved.

The Medical Image Obtaining Process:

As described at step S101 in FIG. 2, the image obtaining function 352 is configured to obtain the medical images including the three-dimensional morphological information about biological tissues (the aortic valve and the ascending aorta) to be processed, in response to the medical image obtaining operation received via the input interface 32. For example, the image obtaining function 352 obtains a CT image three-dimensionally taken of the aortic valve and the ascending aorta.

In this situation, the operation of the medical image obtaining process at step S101 may be started according to a user instruction received via the input interface 32 as described above. Alternatively, the process may be started automatically. In that situation, for example, the image obtaining function 352 is configured to monitor the medical image storage apparatus 2 so as to automatically obtain a medical image every time a new medical image is stored.

In this situation, the image obtaining function 352 may be configured to judge a newly-stored medical image on the basis of an obtainment condition set in advance so as to perform the obtaining process when the medical image satisfies the obtainment condition. For example, the storage circuitry 34 may store therein the obtainment condition that makes it possible to determine a state of the medical image, so that the image obtaining function 352 performs the judging process on the newly-stored medical image on the basis of the obtainment condition stored in the storage circuitry 34.

In an example, as the obtainment condition, the storage circuitry 34 may store therein "medical images taken under an imaging protocol related to the heart should be obtained", "medical images resulting from an enlarged reconstruction should be obtained", or a combination of these two. The image obtaining function 352 is configured to obtain the medical images that satisfy the obtainment condition.

The Structure-of-Interest Extracting Process:

As described at step S102 in FIG. 2, the extracting function 353 is configured to extract the structure of interest from the medical image. More specifically, the extracting function 353 is configured to obtain coordinate information of pixels representing the aortic valve in the CT image. In this situation, the extracting function 353 is capable of extracting the structure of interest by using any of various methods. For example, the extracting function 353 is capable of extracting a region designated within the CT image via the input interface 32 as the structure of interest. In other words, the extracting function 353 is configured to extract the region manually designated by the user as the structure of interest.

Further, for example, by using a known region extracting technique, the extracting function 353 is capable of extracting the structure of interest on the basis of anatomical structures rendered in the CT image. For example, the extracting function 353 may extract the structure of interest from the CT image, by using Otsu's binarization method based on CT values, a region growing method, a snake method, a graph cut method, a mean shift method, or the like.

In another example, the extracting function 353 is capable of extracting the structure of interest from the CT image, by using a trained model constructed on the basis of learning data prepared in advance by using a machine learning technique (which may be deep learning).

In this situation, when processes are performed by implementing the graph cut method or the like on the entire image, there is a possibility that calculation costs may become excessively high. To cope with this situation, the extracting function 353 may perform the extracting process on a region (hereinafter, "relevant region") that is relevant to the structure of interest and is larger than the structure of interest but is smaller than the entire image. For example, when the structure of interest is the aortic valve, the extracting function 353 may identify a heart region, the left ventricle, and a region in the surroundings of the left ventricle, as a relevant region. Further, the extracting function 353 is configured to extract the region of interest by applying the abovementioned extracting process only to the identified relevant region. Alternatively, the relevant region may manually be set by using the input interface 32.

The Surrounding Structure Extracting Process:

As described at step S103 in FIG. 2, the extracting function 353 is configured to extract the surrounding structure positioned in the surroundings of the structure of interest from the medical image. More specifically, the extracting function 353 is configured to obtain coordinate information of pixels representing the ascending aorta in the CT image. For example, the extracting function 353 is configured to extract the surrounding structure by performing a process similar to the structure-of-interest extracting process at step S102. In this situation, the surrounding structure may be set in advance with respect to each structure of interest on the basis of anatomical structures or may be designated by the user every time the process is performed. Alternatively, the surrounding structure may be extracted by the extracting function 353, on the basis of continuity or a distribution of pixel values in the surroundings of the structure of interest.

Further, the surrounding structure set with respect to the structure of interest may arbitrarily be selected. For instance, in the present embodiment, the example is explained in which the ascending aorta is set as the surrounding structure of the aortic valve (the structure of interest). However, the left ventricular outflow tract (LVOT), the left ventricle, or an entire sinus of Valsalva may be determined as the surrounding structure. Further, the surrounding structure set with respect to the structure of interest may be set in the same anatomical structure. For example, it is acceptable to determine a plane (called a "Nadir plane") that is in contact with all the sets of coordinates (called "Nadir") of the points positioned closest to the LVOT side in the valve cusps (the right coronary cusp [RCC]; the left coronary cusp [LCC]; and the non coronary cusp [NCC]) of the aortic valve as the structure of interest and to determine a plane based on the position of the commissure as the surrounding structure.

The Blood Flow Direction Calculating Process:

As described at step S104 in FIG. 2, the first calculating function 354 is configured to calculate the blood flow direction in the structure of interest extracted by the extracting function 353. Further, the second calculating function 355 is configured to calculate the blood flow direction in the surrounding structure extracted by the extracting function 353. Next, examples of these processes will sequentially be explained.

Figure 3A:
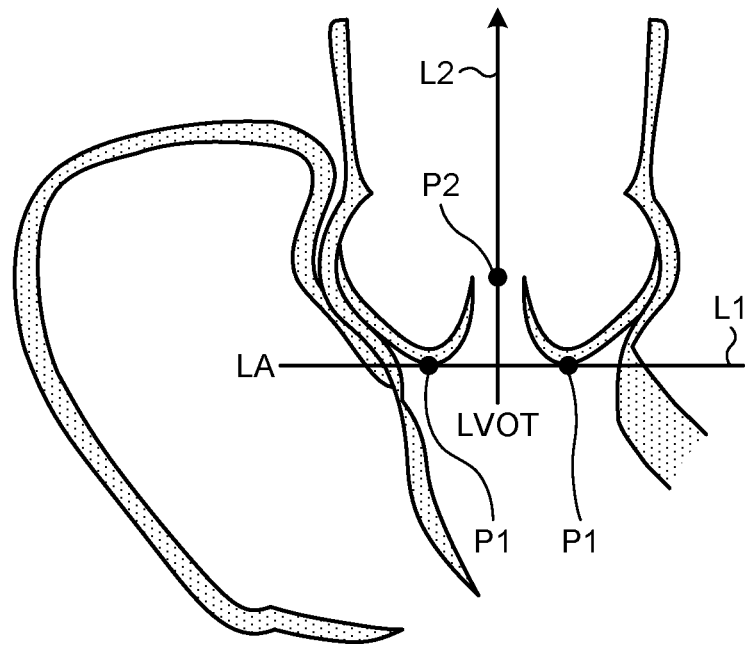
FIG. 3A is a drawing for explaining an example of a process performed by a first calculating function according to the first embodiment.
Figure 3B:
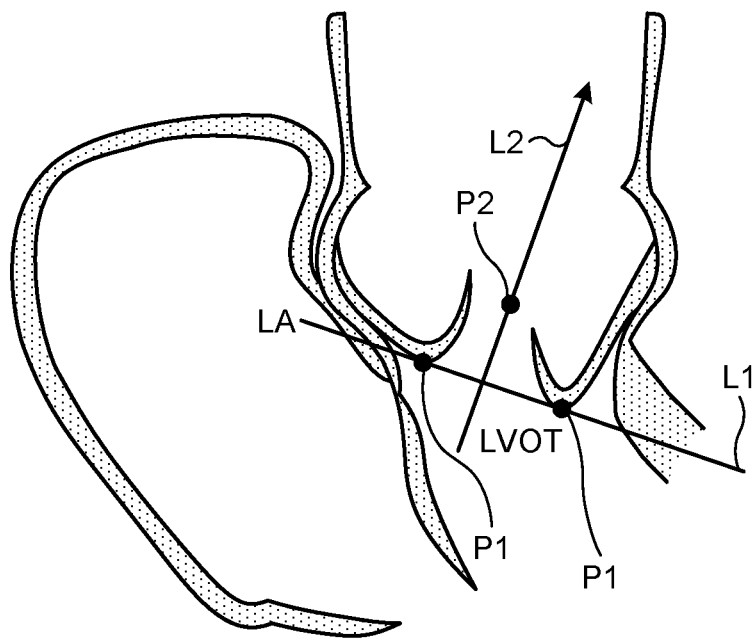
FIG. 3B is a drawing for explaining another example of the process performed by the first calculating function according to the first embodiment.

The first calculating function 354 is configured to calculate the blood flow direction (the first blood flow direction) in the region of interest, on the basis of the structure of the region of interest (the structure of interest). For example, the first calculating function 354 is configured to calculate the blood flow direction caused by the aortic valve, on the basis of the structure of the aortic valve extracted by the extracting function 353. FIGS. 3A and 3B are drawings for explaining examples of the process performed by the first calculating function 354 according to the first embodiment. FIG. 3A illustrates a blood flow direction caused by a normal aortic valve. FIG. 3B illustrates a blood flow direction cause by an abnormal aortic valve.

For example, as illustrated in FIG. 3A, the first calculating function 354 extracts the coordinates (Nadir) "P1" of the point positioned closest to the LVOT side in each of the valve cusps (RCC, LCC, and NCC) of the aortic valve extracted from the CT image. Although FIG. 3A illustrates only two "P1" s, in actuality "P1" is extracted with respect to each of the three valve cusps. Further, the first calculating function 354 extracts a plane (the Nadir plane) "L1" that is in contact with all the three extracted "P1" s.

Further, the first calculating function 354 extracts the orifice of the aortic valve and identifies the coordinates based on the shape of the extracted orifice. For example, as illustrated in FIG. 3A, the first calculating function 354 identifies the position of the center of gravity "P2" of the orifice of the aortic valve. After that, the first calculating function 354 calculates the direction of an arrow "L2" that is perpendicular to the plane "L1" and passes through the position of the center of gravity "P2", as the blood flow direction based on the structure of the aortic valve.

In this situation, with the normal aortic valve, the arrow "L2" illustrated in FIG. 3A indicates the blood flow direction based on the structure of the aortic valve. In contrast, with the abnormal aortic valve, as illustrated in FIG. 3B, the blood flow direction (the arrow "L2") calculated by the first calculating function 354 reflects the structure of the aortic valve and is very different from the blood flow direction calculated for the normal aortic valve.

The method described above is merely an example, and it is acceptable to use any calculation method based on the structure of the region of interest. For example, the first calculating function 354 may extract a plane that passes through the commissure of the aortic valve so as to calculate a blood flow direction based on the structure of the aortic valve, on the basis of the extracted plane and the position of the center of gravity of the orifice. In another example, the first calculating function 354 may identify a plane having a minimum sum of distances from positions on three-dimensional closed curves expressing the annulus and the valve cusps of the aortic valve, so as to calculate a blood flow direction based on the structure of the aortic valve on the basis of the plane and the position of the center of gravity of the orifice. In yet another example, the first calculating function 354 may identify a plane on the basis of the shape of the entire valve, so as to calculate a blood flow direction based on the structure of the aortic valve, on the basis of the plane and the position of the center of gravity of the orifice.

Further, in the examples described above, the blood flow direction is calculated on the basis of the relationship between a plane and a feature point (the position of the center of gravity). However, it is also acceptable to perform the calculation by using a plurality of feature points or to perform the calculation on the basis of a relationship between a line segment and a feature point. For example, it is possible to determine the direction of a straight line passing through the position of the center of gravity of the shape of the entire valve and the position of the center of gravity of the orifice shape, as a blood flow direction based on the structure of the aortic valve.

Figure 4:
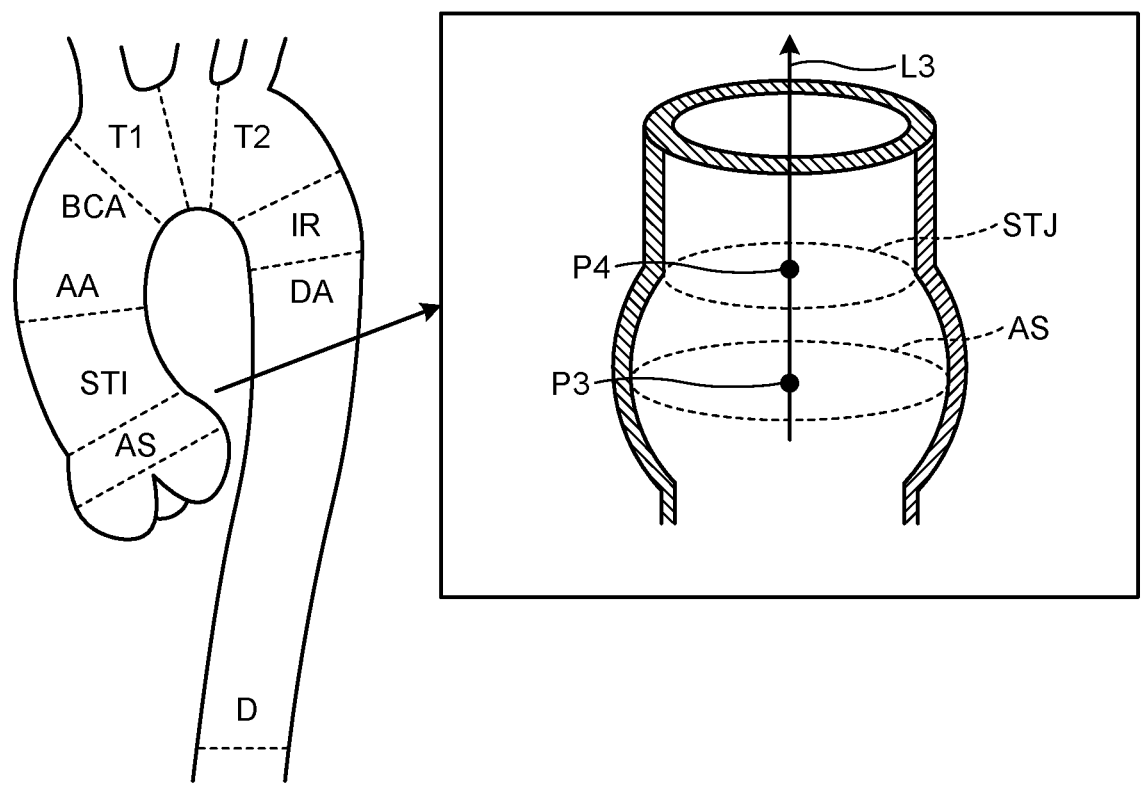
FIG. 4 is a drawing for explaining an example of a process performed by a second calculating function according to the first embodiment.

The second calculating function 355 is configured to calculate the blood flow direction (the second blood flow direction) in the surroundings of the region of interest, on the basis of the structure in the surroundings of the region of interest (the surrounding structure). For example, the second calculating function 355 is configured to calculate the blood flow direction caused by the ascending aorta, on the basis of the structure of the ascending aorta extracted by the extracting function 353. FIG. 4 is a drawing for explaining an example of a process performed by the second calculating function 355 according to the first embodiment.

For example, as illustrated in FIG. 4, the second calculating function 355 extracts the position of the aortic sinus (AS) in the ascending aorta extracted from the CT image and identifies the center position (or the position of the center of gravity) "P3" of a cross-sectional structure at the extracted position. Further, for example, the second calculating function 355 extracts, as illustrated in FIG. 4, the position of the sinotubular junction (STJ) in the ascending aorta extracted from the CT image and identifies the center position (or the position of the center of gravity) "P4" of a cross-sectional structure at the extracted position. Further, the second calculating function 355 calculates the direction of an arrow "L3" passing through "P3" and "P4" that were identified, as the blood flow direction based on the structure of the ascending aorta.

The method described above is merely an example. It is acceptable to use any method as long as the blood flow direction is estimated on the basis of a structure that is in the surroundings of the structure of interest and is other than the structure of interest. For example, the blood flow direction based on the structure of the ascending aorta may be calculated by using the center position or the position of the center of gravity of an LVOT region or a left ventricular region or may be calculated on the basis of the entrance (an opening) of the coronary artery. Alternatively, the blood flow direction based on the structure of the ascending aorta may be calculated on the basis of the curvature of the centerline of the ascending aorta.

The Condition Identifying Process:

As described at step S105 in FIG. 2, the identifying function 356 is configured to identify a condition of the region of interest, on the basis of the blood flow direction (the first blood flow direction) in the structure of interest and the blood flow direction (the second blood flow direction) in the surrounding structure. More specifically, the identifying function 356 is configured to identify the condition of the region of interest, on the basis of the difference between the first blood flow direction and the second blood flow direction. For example, the identifying function 356 is configured to determine that the larger the difference between the first blood flow direction and the second blood flow direction is, the larger adverse impact is imposed on the human body by the structure of the region of interest.

In this situation, the difference between the first blood flow direction and the second blood flow direction may be calculated as an angle formed by the blood flow direction based on the structure of interest and the blood flow direction based on the surrounding structure or calculated as a minimum distance between a straight line indicating the blood flow direction based on the structure of interest and a straight line indicating the blood flow direction based on the surrounding structure. The identifying function 356 is configured to determine that the larger the difference between the blood flow directions is, the worse is the condition. In other words, when the blood flow direction estimated from the structure of interest is more similar to the blood flow direction based on the structure in the surroundings of the structure of interest, the blood flows more smoothly. Accordingly, the identifying function 356 is configured to determine that the condition is better (i.e., the risk is lower) when the two types of blood flow directions are closer to each other (i.e., the angle formed by the two is smaller, or the distance therebetween is shorter).

FIGS. 5A to 5D are drawings for explaining examples of the identifying process performed by the identifying function 356 according to the first embodiment. FIGS. 5A to 5D illustrate the identifying process based on the first blood flow direction (the arrow "L2") calculated while using the aortic valve as the structure of interest and the second blood flow direction (the arrow "L3") calculated while using the ascending aorta as the surrounding structure. Further, FIGS. 5A to 5D illustrate the examples in which a judging process is performed, on the basis of the angle formed by the blood flow direction based on the structure of interest and the blood flow direction based on the surrounding structure.

Figure 5A:
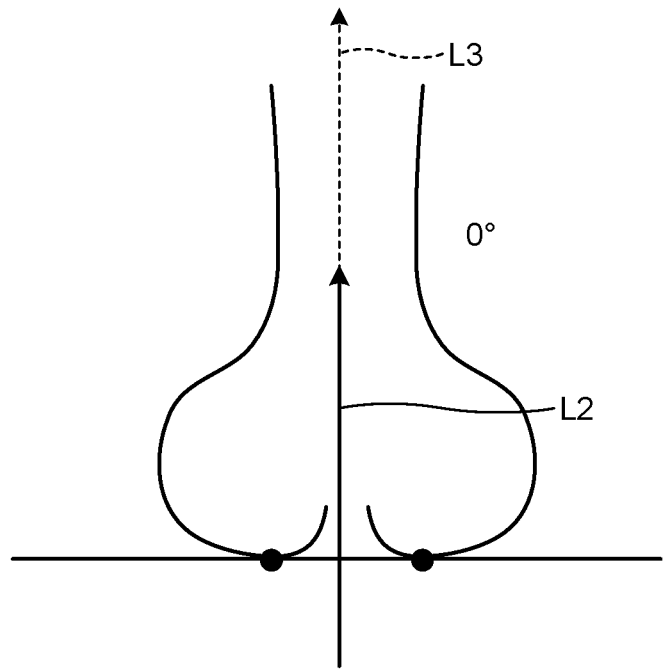
FIG. 5A is a drawing for explaining an example of an identifying process performed by an identifying function according to the first embodiment.

For example, as illustrated in FIG. 5A, when the angle formed by the blood flow direction (the arrow "L2") at the aortic valve and the blood flow direction (the arrow "L3") in the ascending aorta is "0°", the identifying function 356 determines that "the risk imposed on the human body by the aortic valve is low". In another example, as illustrated in FIG. 5B, when the angle formed by the blood flow direction (the arrow "L2") at the aortic valve and the blood flow direction (the arrow "L3") in the ascending aorta is "30°", the identifying function 356 determines that "the aortic valve imposes a certain risk on the human body".

Figure 5B:
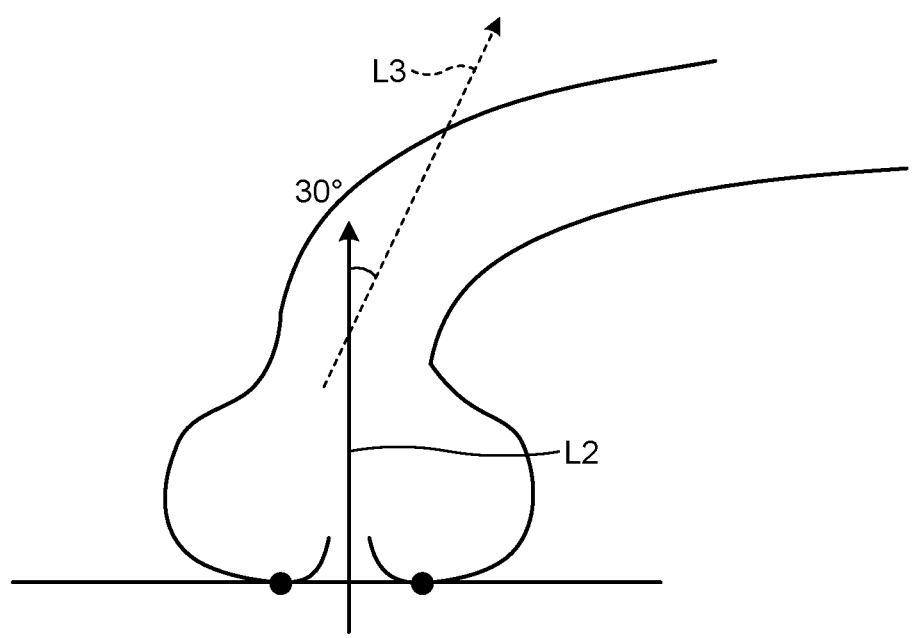
FIG. 5B is a drawing for explaining another example of the identifying process performed by the identifying function according to the first embodiment.

Between the condition illustrated in FIG. 5A and the condition illustrated in FIG. 5B, the shape of the aortic valve is the same, and the blood flow direction (the arrow "L2") is the same, but because the shapes of the ascending aorta are different, the judgment results are different.

In this situation, when calculating the angle formed by the straight line indicating the blood flow direction based on the structure of interest and the straight line indicating the blood flow direction based on the surrounding structure, the identifying function 356 is configured to calculate the formed angle, by projecting the straight lines from predetermined directions. In one example, the identifying function 356 is configured to calculate the formed angle, by projecting the straight lines after determining the projection directions so as to maximize the angle formed by the straight line indicating the blood flow direction based on the structure of interest and the straight line indicating the blood flow direction based on the surrounding structure. Alternatively, the formed angle may be calculated on the basis of three-dimensional vectors of the straight lines.

Figure 5C:
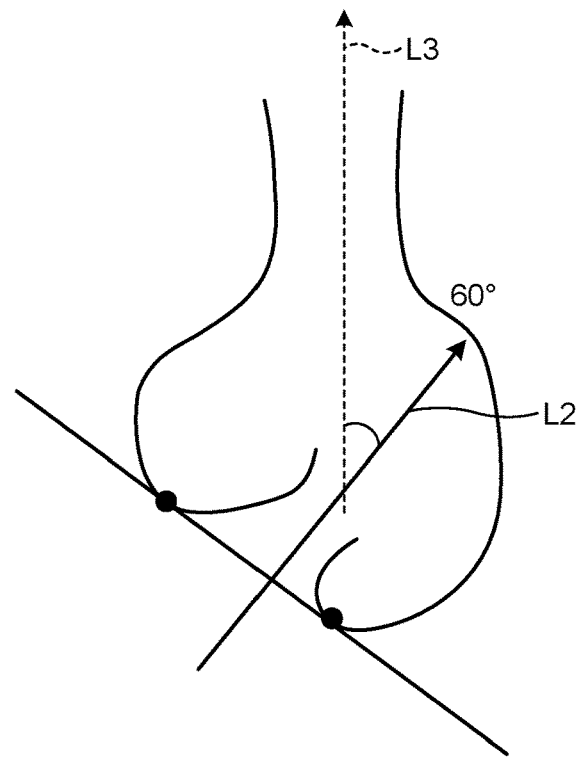
FIG. 5C is a drawing for explaining yet another example of the identifying process performed by the identifying function according to the first embodiment.
Figure 5D:
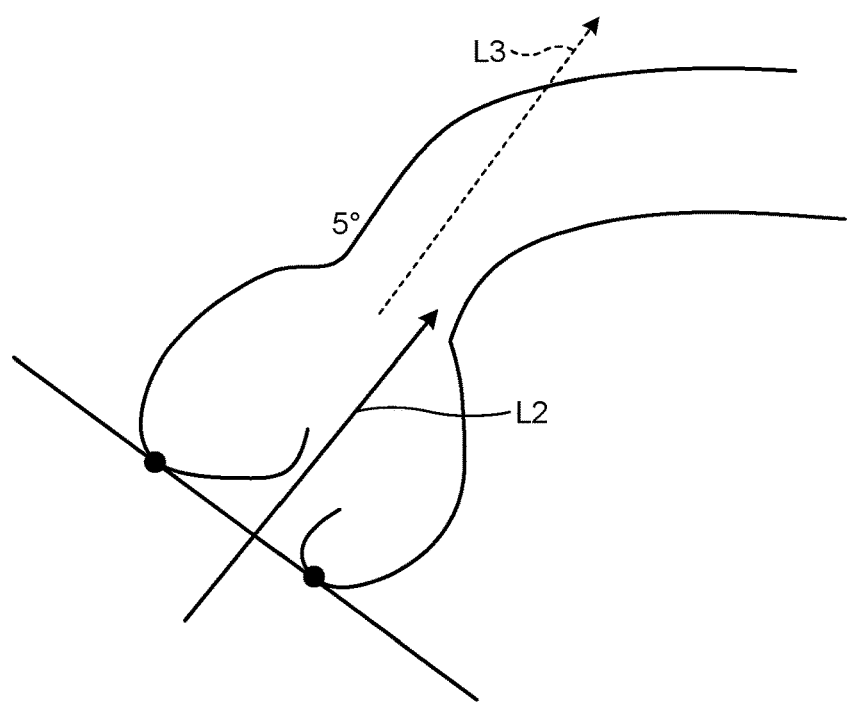
FIG. 5D is a drawing for explaining yet another example of the identifying process performed by the identifying function according to the first embodiment.

Similarly, in yet another example, as illustrated in FIG. 5C, when the angle formed by the blood flow direction (the arrow "L2") at the aortic valve and the blood flow direction (the arrow "L3") in the ascending aorta is "60°", the identifying function 356 determines that "the risk imposed on the human body by the aortic valve is high". In yet another example, as illustrated in FIG. 5D, when the angle formed by the blood flow direction (the arrow "L2") at the aortic valve and the blood flow direction (the arrow "L3") in the ascending aorta is "5°", the identifying function 356 determines that "the risk imposed on the human body by the aortic valve is low". As explained herein, in the judgment results from the conditions illustrated in FIGS. 5C and 5D also, the judgment results are different because the shapes of the ascending aorta are different.

In this situation, the identifying function 356 may read, from the storage circuitry 34, correspondence information that is set in advance with a correspondence relationship between various conditions of the blood flow directions with each other and magnitudes of the risk, so as to use the read information in the judging process. FIG. 6 is a drawing illustrating an example of the correspondence information according to the first embodiment. In the correspondence information in FIG. 6, angles formed by the blood flow directions are kept in correspondence, as the conditions of the blood flow directions. For example, as illustrated in FIG. 6, the storage circuitry 34 is configured to store therein the correspondence information keeping disease risks, angles, and warning phrases in correspondence with one another.

For example, the correspondence information keeps the following in correspondence with one another: "Disease risk: high"; "Angle: 45° to 90°"; and "A warning phrase: CHECK FOR PRESENCE OF AORTIC DISEASE. IF NO ABNORMALITY IS FOUND, CONSIDER GIVING DIFFERENT EXAMINATION". When this correspondence information is used as a basis, in the situation where the angle formed by the blood flow direction at the aortic valve and the blood flow direction in the ascending aorta is in the range of "45° to 90°", the identifying function 356 determines that the disease risk is "high", on the basis of the correspondence information. Further, the warning phrase in the correspondence information is referenced at the time of displaying an evaluation result of the judging process based on the blood flow directions.

Similarly, the correspondence information keeps other angle ranges, disease risks for the angle ranges, and warning phrases for the angle ranges in correspondence with one another, so that the correspondence information can be used for the judging process based on the blood flow directions and for displaying the evaluation information.

The Evaluation Information Display Process:

As described at step S106 in FIG. 2, the controlling function 351 is configured to cause the display 33 to display the evaluation information based on the condition identified by the identifying function 356. More specifically, the controlling function 351 is configured to cause the evaluation information indicating the judgment result obtained by the identifying function 356 to be displayed. For example, the controlling function 351 is configured to cause the display 33 to display information indicating a degree of the disease risk (e.g., high, medium, low, or error) and a warning phrase. In this situation, because the angle formed by the blood flow directions and the distance therebetween are values that increase when the risk is higher, the controlling function 351 may display one or both of these values themselves as the evaluation information.

The display of the evaluation information realized by the controlling function 351 may be implemented by using any of various methods. FIGS. 7A to 7C are drawings illustrating examples of the evaluation information according to the first embodiment. For example, as illustrated in FIG. 7A, the controlling function 351 may display evaluation information including a judgment result "medium" related to the disease risk and the warning phrase in the form of text. In this situation, on the basis of the degree of the condition of the region of interest, the controlling function 351 is capable of changing the display mode of the evaluation information. For example, the controlling function 351 may emphasize the display by changing the color, the font, and/or the size of the text in correspondence with the degrees (high, medium, or low) of the disease risk.

Further, the controlling function 351 is also capable of causing the evaluation information to be displayed over the medical image. For example, as illustrated in FIG. 7B, the controlling function 351 is also capable of causing text indicating the degree of the risk and the value (the angle or the distance) calculated at step S105 to be displayed while being superimposed over the CT image obtained at step S101. Further, the controlling function 351 is also capable of causing the information indicating the blood flow directions calculated at step S104 to be displayed over the CT image. For example, as illustrated in FIG. 7B, the controlling function 351 may cause the arrow L2 indicating the blood flow direction in the structure of interest and the arrow L3 indicating the blood flow direction in the surrounding structure to be displayed over the CT image. In this situation, the controlling function 351 is capable of displaying the straight lines while varying the display modes thereof (e.g., by using different colors). Further, the controlling function 351 is also capable of identifying cross-sectional planes expressing the angle formed by the two calculated blood flow directions, so as to display the cross-sectional planes first before displaying the blood flow directions in a superimposed manner. Further, the controlling function 351 is also capable of displaying arrows indicating the blood flow directions so as to be projected on cross-sectional planes positioned in arbitrary directions.

Further, as illustrated in FIG. 7C, the controlling function 351 is also capable of displaying the evaluation information over a CT image (a VR image, an SR image, or the like) displayed three-dimensionally. Because the blood flow directions are calculated three-dimensionally in principle, visibility thereof is enhanced when being displayed over a three-dimensional image.

As explained above, the controlling function 351 is capable of displaying the evaluation information in any of the various modes. In this situation, when the evaluation information is displayed as described above, it is possible to arbitrary change the display mode such as the size of the displayed text, as well as the thicknesses, colors, and/or transparency levels of the arrows, in accordance with the magnitude of the disease risk. Further, the display of the evaluation information at step S106 may be implemented automatically after the condition is identified.

Alternatively, the display may explicitly be realized as a result of the user selecting a button (not illustrated) or the like.

First Modification Example

In the embodiment described above, at step S104, the blood flow directions are calculated (estimated) on the basis of only the structure of the region of interest and the structure in the surroundings of the region of interest. However, possible embodiments are not limited to this example. For instance, characteristics of the valve estimated from information such as an image may be taken into consideration. In that situation, for example, the first calculating function 354 may be configured to estimate the presence/absence and the amount of calcification or the firmness or the thickness of each of the structures on the basis of magnitudes of pixel values of the pixels corresponding to the region of interest, so as to calculate the blood flow directions while further taking these elements into consideration.

Second Modification Example

In the embodiment described above, at step S104, the geometrical features are calculated on the basis of the structure of the region of interest and the structure in the surroundings of the region of interest, so as to calculate (estimate) the blood flow directions on the basis of these features. However, possible embodiments are not limited to this example. For instance, a blood flow state may be simulated and calculated by using a known fluid simulation technique. For example, an electric circuit model simulating circulatory dynamics in the subject's body may be designed in advance on the basis of a Windkessel model or a pulse wave propagation model, so that the first calculating function 354 and the second calculating function 355 are able to obtain blood flow information of the structures by inputting the structure of the region of interest and the structure in the surroundings of the region of interest to the electric circuit model. Alternatively, instead of the electric circuit model, the first calculating function 354 and the second calculating function 355 are also capable of calculating targeted fluid information using numerical values, by preparing necessary simultaneous equations such as Navier-Stoke equations, equations of continuity, Maxwell equations, state equations, or the like and inputting various types of parameters to the equations.

Further, when performing the simulation described above, it is also acceptable to calculate blood flow directions by virtually configuring the following structure: The blood flow direction based on the structure of interest may be estimated only from the structure of interest (i.e., without using any information about the structure in the surroundings of the structure of interest) or may be calculated by applying a generic human body structure to the surrounding structure. The generic human body structure is prepared as a model in advance from a large amount of data, so that only a magnification ratio for the size can be corrected in accordance with the size of the structure of interest. Further, the blood flow state based on the surrounding structure may be estimated only from the surrounding structure (i.e., without using any information about the structure of interest) or may be calculated by applying a generic human body structure to the structure of interest. In this situation, the generic human body structure is prepared as a model in advance from a large amount of data, so that only a magnification ratio for the size can be corrected in accordance with the size of the structure of interest. In this manner, it is possible to calculate the blood flow state dependent on the structure of interest or the surrounding structure.

As described above, according to the first embodiment, the image obtaining function 352 is configured to obtain the medical image. The first calculating function 354 is configured to calculate the first blood flow direction on the basis of the structure of the region of interest rendered in the medical image. The second calculating function 355 is configured to calculate the second blood flow direction on the basis of the structure in the surroundings of the region of interest. The identifying function 356 is configured to identify the condition of the region of interest on the basis of the first blood flow direction and the second blood flow direction. Consequently, the medical image processing apparatus 3 according to the first embodiment is capable of identifying the condition of the region of interest while taking the structure in the surroundings of the region of interest into consideration and thus makes it possible to appropriately estimate the condition of the region of interest. As a result, the medical image processing apparatus 3 makes it possible to correctly estimate the degree of the abnormality or the prognostic risk which may be caused by the organ subject to the analysis.

Further, according to the first embodiment, the identifying function 356 is configured to identify the condition of the region of interest, on the basis of the difference between the first blood flow direction and the second blood flow direction. Consequently, the medical image processing apparatus 3 according to the first embodiment is capable of identifying the condition of the region of interest on the basis of whether or not the blood flow is smooth and thus makes it possible to make the estimates with a higher level of precision.

Also, according to the first embodiment, the identifying function 356 is configured to determine that the larger the difference between the first blood flow direction and the second blood flow direction is, the larger adverse impact is imposed on the human body by the structure of the region of interest. Consequently, the medical image processing apparatus 3 according to the first embodiment makes it possible to precisely determine the disease risk and the degree of the abnormality.

Furthermore, according to the first embodiment, the controlling function 351 is configured to cause the display 33 to display the evaluation information based on the condition of the region of interest. Consequently, the medical image processing apparatus 3 according to the first embodiment makes it possible to provide the user with the evaluation information.

In addition, according to the first embodiment, the controlling function 351 is configured to change the display mode of the evaluation information on the basis of the degree of the condition of the region of interest. Consequently, the medical image processing apparatus 3 according to the first embodiment makes it possible to provide the user with the information corresponding to the disease risk and the degree of the abnormality.

Further, according to the first embodiment, the controlling function 351 is configured to cause the evaluation information to be displayed over the medical image. Consequently, the medical image processing apparatus 3 according to the first embodiment makes it possible to provide the information about the anatomical structures, together with the evaluation information.

Furthermore, according to the first embodiment, the controlling function 351 is configured to cause the information indicating the first blood flow direction and the information indicating the second blood flow direction to be displayed over the medical image. Consequently, the medical image processing apparatus 3 according to the first embodiment makes it possible for viewers to visually recognize the information about the anatomical structures and the blood flow directions caused thereby.

Second Embodiment

Figure 8:
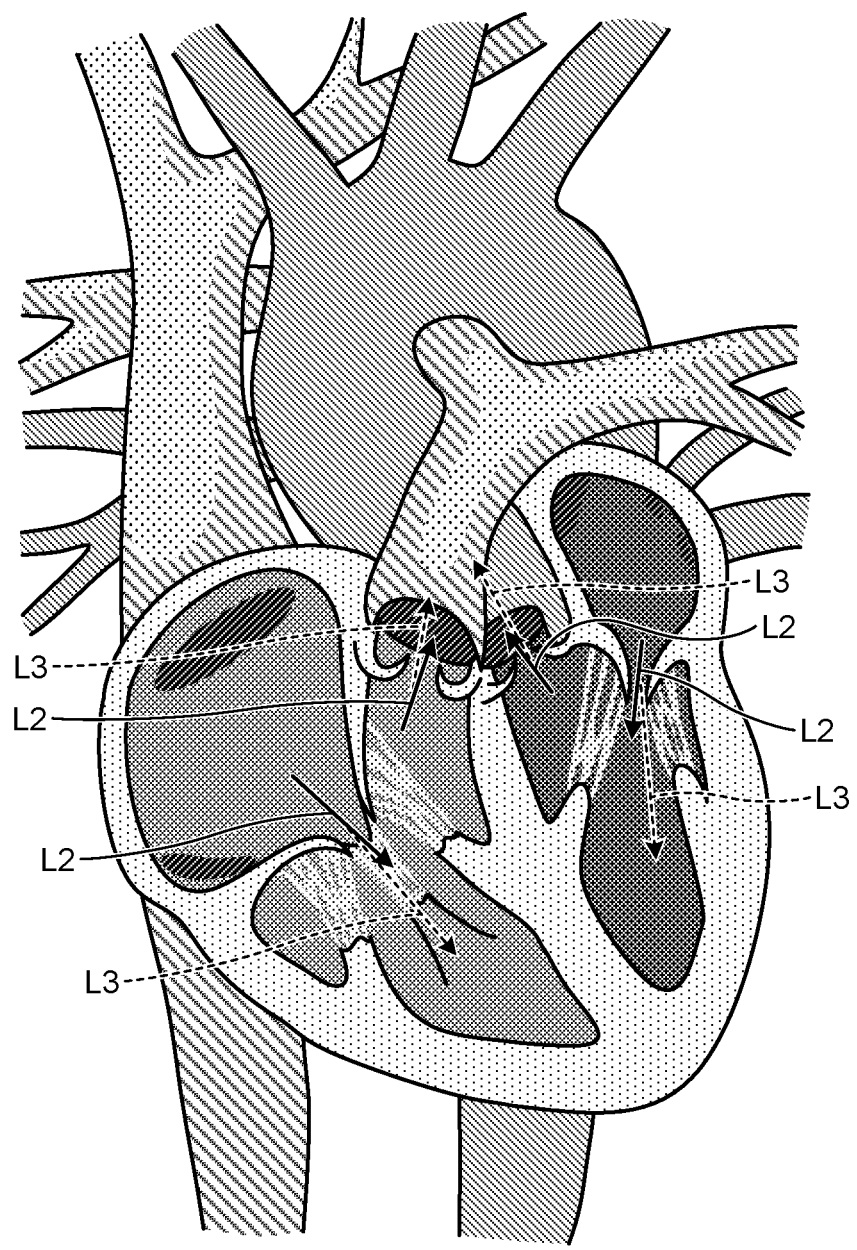
FIG. 8 is a drawing for explaining a process according to a second embodiment.

In the first embodiment above, the example using the single region of interest was explained. In a second embodiment, an example using a plurality of regions of interest will be explained. In the second embodiment, an example using four valves, namely the aortic valve, the mitral valve, the tricuspid valve, and the pulmonary valve, as the plurality of regions of interest will be explained. FIG. 8 is a drawing for explaining a process according to the second embodiment.

For example, at step S102, the extracting function 353 according to the second embodiment extracts regions each representing a different one of the aortic, mitral, tricuspid, and pulmonary valves, from a CT image rendering the entire heart and various types of blood vessels illustrated in FIG. 8. Further, at step S103, the extracting function 353 extracts, for example, the ascending aorta as a surrounding structure of the aortic valve and further extracts the left atrium and the left ventricle as surrounding structures of the mitral valve. In addition, the extracting function 353 extracts the right atrium and the right ventricle as surrounding structures of the tricuspid valve and further extracts the pulmonary artery as a surrounding structure of the pulmonary valve. In this situation, the extraction method used at steps S102 and S103 is the same as that used in the first embodiment.

After that, at step S104, the first calculating function 354 and the second calculating function 355 according to the second embodiment calculate blood flow directions (the arrows L2 in FIG. 8) based on the valve structures and blood flow directions (the arrows L3 in FIG. 8) based on the surrounding structures in correspondence with the respective valves. In this situation, it is possible to perform the calculation on the pulmonary valve in the same manner as in the first embodiment. In contrast, with respect to the mitral valve and the tricuspid valve, for example, the first calculating function 354 calculates a blood flow direction based on the structure of interest as the first blood flow direction, on the basis of a line segment that is perpendicular to the line segment connecting together the left and the right commissures and that passes through the center of gravity of the orifice. The second calculating function 355 calculates a blood flow direction based on the surrounding structure as the second blood flow direction, on the basis of a line segment connecting the center of gravity of the left atrium to the center of gravity of the left ventricle or a line segment connecting the center of gravity of the right atrium to the center of gravity of the right ventricle. These calculation methods are merely examples, and it is acceptable to use other calculation methods, as appropriate.

Subsequently, the identifying function 356 according to the second embodiment identifies the condition of each of the corresponding structures of interest on the basis of the first blood flow direction and the second blood flow direction with respect to each of the regions of interest and further identifies the condition of a region made up of the plurality of regions of interest on the basis of the identified conditions of the structures of interest. In other words, at step S105, by using the arrows L2 and the arrows L3 corresponding to the valves, the identifying function 356 calculates values (angles formed by the blood flow directions or the distances therebetween) each indicating the degree of the condition (a risk) of the corresponding valve and further calculates a predetermined single statistical value (a total value, an average value, or the like), on the basis of the values indicating the degrees of the conditions (the risks) corresponding to all the valves, so as to determine the statistical value as a risk of the subject. As a result, it is possible to determine the disease risk of the entire heart.

After that, at step S106, the controlling function 351 according to the second embodiment causes evaluation information (e.g., a judgment result regarding the disease risk) based on the judgment result obtained by the identifying function 356 to be displayed. In this situation, the controlling function 351 is also capable of causing a blood flow state based on all of the structures of interest and the surrounding structures to be displayed over a three-dimensional image and is also capable of causing the same to be displayed with a schematic drawing. Further, the controlling function 351 is also capable of displaying a risk based on each of the structures separately for each structure and is also capable of displaying only the statistical value.

As explained above, according to the second embodiment, the first calculating function 354 is configured to calculate the first blood flow direction with respect to each of the plurality of regions of interest rendered in the medical image. With respect to each of the plurality of regions of interest, the second calculating function 355 is configured to calculate the second blood flow direction in the structure in the surroundings thereof. The identifying function 356 is configured to identify the condition of each of the regions of interest on the basis of the first blood flow directions and the second blood flow directions and to further identify the condition of the region made up of the plurality of regions of interest, on the basis of the condition identified with respect to each of the regions of interest. Consequently, the medical image processing apparatus 3 according to the second embodiment makes it possible to comprehensively evaluate the condition (the degree of the abnormality, the prognostic risk, or the like) of the biological organ structured with the plurality of regions of interest, on the basis of the conditions of the regions of interest.

Third Embodiment

In the first embodiment described above, the example using the medical image at the single point in time was explained. In a third embodiment, an example will be explained in which the condition of a region of interest is identified by using medical images corresponding to a plurality of points in time. In this situation, the image obtaining function 352 according to the third embodiment is configured to obtain the plurality of medical images taken at the mutually-different points in time. The first calculating function 354 according to the third embodiment is configured to calculate the first blood flow direction based on the structure of the region of interest with respect to each of the medical images corresponding to the mutually-different points in time. The second calculating function 355 according to the third embodiment is configured to calculate the second blood flow direction based on the surrounding structure, with respect to each of the medical images corresponding to the mutually-different points in time. The identifying function 356 according to the third embodiment is configured to calculate the difference between the first blood flow direction and the second blood flow direction with respect to each of the medical images corresponding to the mutually-different points in time and to further identify the condition of the region of interest on the basis of the difference calculated with respect to each of the mutually-different points in time.

Figure 9:
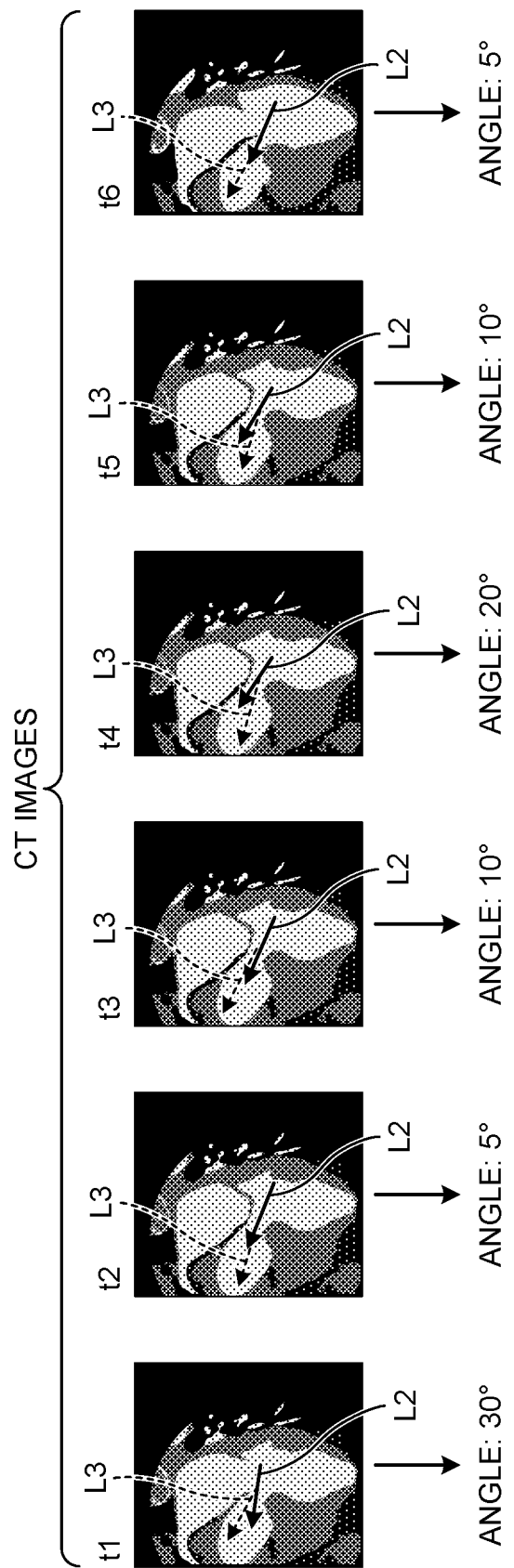
FIG. 9 is a drawing for explaining an example of a process according to a third embodiment.

FIG. 9 is a drawing for explaining an example of a process according to the third embodiment. For example, at step S101, the image obtaining function 352 obtains four-dimensional (4D) CT images taken at the points in time t1 to t6 indicated in FIG. 9.

After that, at step S102, the extracting function 353 extracts mutually the same structure of interest (e.g., the aortic valve) from each of the CT images corresponding to the mutually-different points in time and, at step S103, extracts mutually the same surrounding structure (e.g., the ascending aorta) from each of the CT images corresponding to the mutually-different points in time.

Subsequently, at step S104, the first calculating function 354 calculates blood flow directions (the arrows L2 in FIG. 9) based on the structure of interest, whereas the second calculating function 355 calculates blood flow directions (the arrows L3 in FIG. 9) based on the surrounding structure.

Further, at step S105, the identifying function 356 calculates a value (an angle in the example of FIG. 9) indicating a degree of the condition (a risk) with respect to each of the CT images corresponding to the mutually-different points in time. Further, the identifying function 356 calculates a predetermined single statistical value (a total value, a variance value, or the like) from the values each indicating the degree of the condition (the risk) based on the corresponding one of the CT images and determines the statistical value as a condition (a risk) of the subject. For example, by using a variance value, it is possible to analyze the relationship between the blood flow state caused by the valve structure and the blood flow state caused by the structure in the surroundings of the valve on the basis of a change amount within one heartbeat. It is therefore acceptable to determine that the risk is lower when the variance value is smaller. In another example, it is also acceptable to determine that the risk is lower when the total value is smaller.

Figure 10:
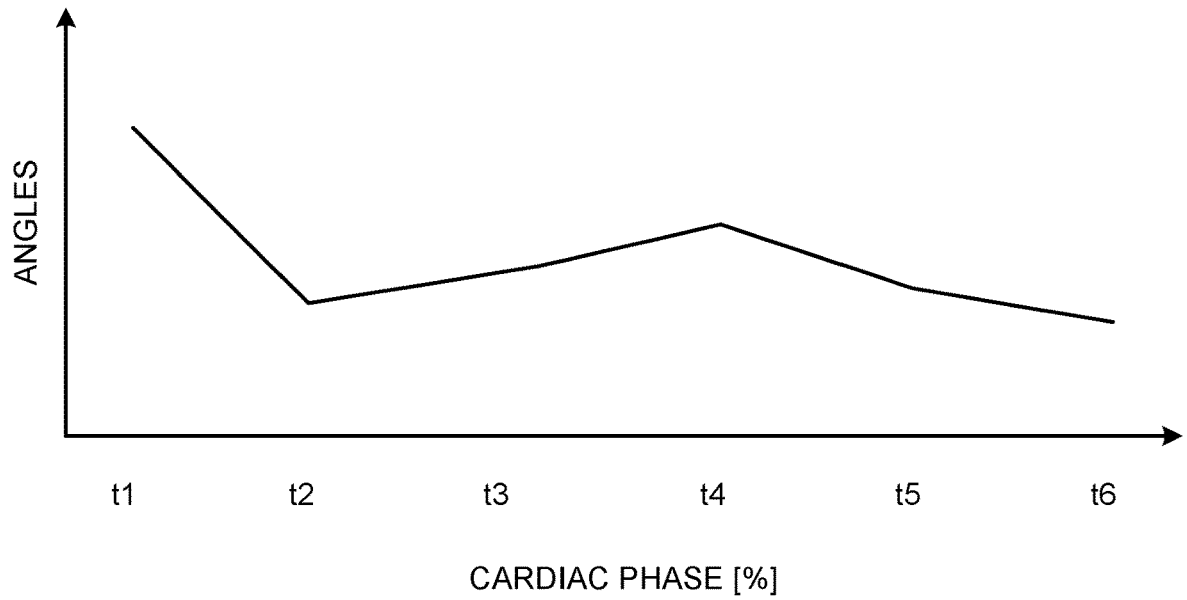
FIG. 10 is a drawing illustrating an example of evaluation information according to the third embodiment.

After that, at step S106, the controlling function 351 causes the evaluation information (e.g., a judgment result indicating a disease risk) based on the judgment result obtained by the identifying function 356 to be displayed. In this situation, the controlling function 351 may display information about chronological changes in the value indicating the degree of the condition. More specifically, the controlling function 351 may display, in a graph, a relationship between pieces of evaluation information based on the conditions of the region of interest identified in mutually-different temporal phases corresponding to the plurality of medical images and the mutually-different temporal phases. FIG. 10 is a drawing illustrating an example of the evaluation information according to the third embodiment. For example, as illustrated in FIG. 10, the controlling function 351 may display a graph in which the horizontal axis expresses points in time of imaging (cardiac phase percentages), while the vertical axis expresses values (angles in FIG. 10) indicating degrees of the condition.

Figure 11:
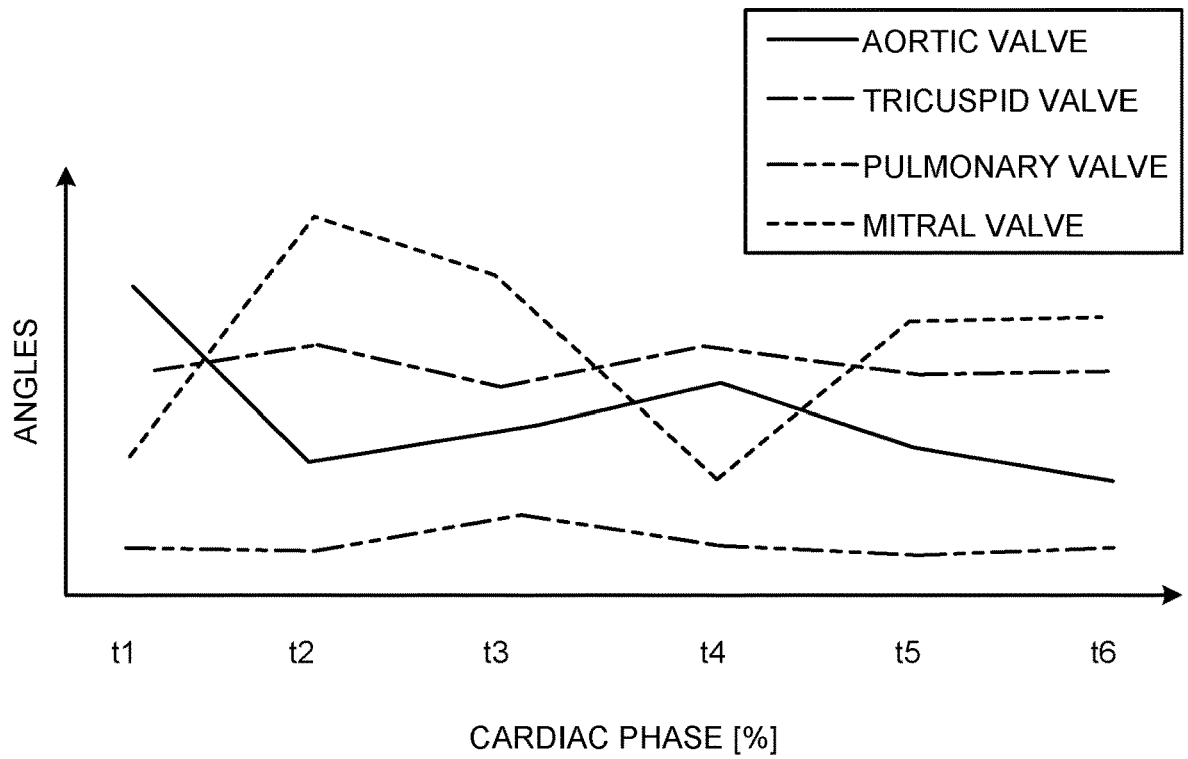
FIG. 11 is a drawing illustrating another example of the evaluation information according to the third embodiment.

Further, the third embodiment may be implemented in combination with the second embodiment. In other words, a plurality of regions of interest may be set with respect to each of the medical images corresponding to a plurality of points in time, so as to perform the judging process with respect to each of the regions of interest. In that situation, for example, as illustrated in FIG. 11, the controlling function 351 may display a graph indicating values (angles in FIG. 11) indicating degrees of the condition at the mutually-different points in time of imaging (cardiac phase percentage), with respect to the aortic valve, the tricuspid valve, the pulmonary valve, and the mitral valve. FIG. 11 is a drawing illustrating the example of the evaluation information according to the third embodiment.

As explained above, according to the third embodiment, the image obtaining function 352 is configured to obtain the plurality of medical images taken at the mutually-different points in time. With respect to each of the medical images corresponding to the mutually-different points in time, the first calculating function 354 is configured to calculate the first blood flow direction based on the structure of the region of interest. With respect to each of the medical images corresponding to the mutually-different points in time, the second calculating function 355 is configured to calculate the second blood flow direction based on the structure in the surroundings. With respect to each of the medical images corresponding to the mutually-different points in time, the identifying function 356 is configured to calculate the difference between the first blood flow direction and the second blood flow direction and to further identify the condition of the region of interest on the basis of the difference calculated with respect to each of the mutually-different points in time. Consequently, the medical image processing apparatus 3 according to the third embodiment is capable of making the estimate while taking the chronological changes in the condition into consideration and thus makes it possible to make the estimate further in detail with regard to the region of interest.

Further, according to the third embodiment, the controlling function 351 is configured to display, in the graph, the relationship between the evaluation information based on the conditions of the region of interest identified in the mutually-different temporal phases corresponding to the plurality of medical images and the temporal phases. Consequently, the medical image processing apparatus 3 according to the third embodiment makes it possible for viewers to visually recognize the chronological changes in the evaluation information.

OTHER EMBODIMENTS

In the embodiments described above, the example was explained in which the evaluation information is displayed on the display 33 of the medical image processing apparatus 3; however, possible embodiments are not limited to this example. For instance, the evaluation information may be displayed on a display of another apparatus connected to the network.

Further, in the above embodiments, the example was explained in which a controlling unit, an image obtaining unit, an extracting unit, a first calculating unit, a second calculating unit, and an identifying unit of the present disclosure are realized as the controlling function, the image obtaining function, the extracting function, the first calculating function, the second calculating function, and the identifying function of the processing circuitry, respectively; however, possible embodiments are not limited to this example. For instance, instead of realizing the controlling unit, the image obtaining unit, the extracting unit, the first calculating unit, the second calculating unit, and the identifying unit of the present disclosure by using the controlling function, the image obtaining function, the extracting function, the first calculating function, the second calculating function, and the identifying function described in the embodiments, these functions may be realized by using hardware alone, software alone, or a combination of hardware and software.

Further, the term "processor" used in the description of the above embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). In this situation, instead of having the programs saved in a storage circuit, it is also acceptable to directly incorporate the programs in the circuit of one or more processors. In that situation, the one or more processors are configured to realize the functions by reading and executing the programs incorporated in the circuitry thereof. Further, the processors of the present embodiments do not each necessarily have to be structured as a single circuit. It is also acceptable to structure one processor by combining together a plurality of independent circuits so as to realize the functions thereof.

A medical image processing program executed by a processor is provided as being incorporated in advance in a Read-Only Memory (ROM), a storage circuit, or the like. The medical image processing program may be provided as being recorded on a non-transitory computer-readable storage medium such as a Compact Disk Read-Only Memory (CD-ROM), a Flexible Disk (FD), a Compact Disk Recordable (CD-R), or a Digital Versatile Disk (DVD), in a file that is in an installable or executable format for the devices. Further, the medical image processing program may be stored in a computer connected to a network such as the Internet so as to be provided or distributed as being downloaded via the network. For example, the medical image processing program is structured with modules including the processing functions described above. In actual hardware, as a result of a CPU reading and executing the medical image processing program from a storage medium such as a ROM, the modules are loaded into a main storage device so as to be generated in the main storage device.

Further, constituent elements of the apparatuses in the drawings of the above embodiments and modification examples are based on functional concepts. Thus, it is not necessarily required to physically configure the constituent elements as indicated in the drawings. In other words, specific modes of distribution and integration of the apparatuses are not limited to those illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a CPU and a program analyzed and executed by the CPU or may be realized as hardware using wired logic.

Further, with regard to the processes explained in the embodiments and the modification examples described above, it is acceptable to manually perform all or a part of the processes described as being performed automatically. Conversely, by using a publicly-known method, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

According to at least one aspect of the embodiments described above, it is possible to appropriately estimate the condition of the region of interest.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
processing circuitry configured to
obtain a medical image;
calculate a first blood flow direction based on a structure of a region of interest rendered in the medical image;
calculate a second blood flow direction based on a structure of a region surrounding the region of interest, the region surrounding the region of interest being different from the region of interest;
determine an angle formed between the first blood flow direction and the second blood flow direction; and
identify information related to a disease risk in the region of interest, based on the determined angle.

2. The medical image processing apparatus according to claim 1, wherein the processing circuitry is further configured to determine that the larger the angle formed between the first blood flow direction and the second blood flow direction is, the larger an adverse impact is imposed on a human body by the structure of the region of interest.

3. The medical image processing apparatus according to claim 1, wherein the processing circuitry is further configured to:
calculate the first blood flow direction with respect to each of a plurality of regions of interest included in the medical image;
calculate the second blood flow direction with respect to a structure of a region surrounding each of the plurality of regions of interest; and
identify information related to the disease risk in each of the regions of interest based on the first blood flow directions and the second blood flow directions, and further identify information related to the disease risk in a region made up of the plurality of regions of interest based on the identified information related to the disease risk with respect to each of the regions of interest.

4. The medical image processing apparatus according to claim 1, wherein the processing circuitry is further configured to:
obtain a plurality of medical images taken at mutually-different points in time;
calculate the first blood flow direction based on the structure of the region of interest, with respect to each of the medical images corresponding to the mutually-different points in time;
calculate the second blood flow direction based on the structure of the region surrounding the region of interest, with respect to each of the medical images corresponding to the mutually-different points in time; and
calculate the angle formed between the first blood flow direction and the second blood flow direction with respect to each of the medical images corresponding to the mutually-different points in time, and identify the information related to the disease risk in the region of interest based on the calculated angle with respect to each of the mutually-different points in time.

5. The medical image processing apparatus according to claim 1, wherein the processing circuitry is further configured to cause a display to display evaluation information based on the information related to the diseased risk in the region of interest.

6. The medical image processing apparatus according to claim 5, wherein the processing circuitry is further configured to change a display mode of the evaluation information based on a degree of the disease risk in the region of interest.

7. The medical image processing apparatus according to claim 5, wherein the processing circuitry is further configured to cause the evaluation information to be displayed over the medical image.

8. The medical image processing apparatus according to claim 7, wherein the processing circuitry is further configured to cause information indicating the first blood flow direction and information indicating the second blood flow direction to be displayed over the medical image.

9. The medical image processing apparatus according to claim 4, wherein the processing circuitry is further configured to display, in a graph, a relationship between the evaluation information based on the information related to the disease risk in the region of interest identified in each of temporal phases corresponding to the plurality of medical images and the temporal phases.

10. A medical image processing method comprising:
obtaining a medical image;
calculating a first blood flow direction based on a structure of a region of interest rendered in the medical image;
calculating a second blood flow direction based on a structure of a region surrounding the region of interest, the region surrounding the region of interest being different from the region of interest;
determining an angle formed between the first blood flow direction and the second blood flow direction; and
identifying information related to a disease risk in the region of interest, based on the determined angle.

11. A storage medium storing therein, in a non-transitory manner, a program that causes a computer to execute processes of:
obtaining a medical image;
calculating a first blood flow direction based on a structure of a region of interest rendered in the medical image;
calculating a second blood flow direction based on a structure of a region surrounding the region of interest, the region surrounding the region of interest being different from the region of interest;
determining an angle formed between the first blood flow direction and the second blood flow direction; and
identifying information related to a disease risk in the region of interest, based on the determined angle.

12. A medical image processing apparatus, comprising:
processing circuitry configured to
obtain a medical image;
calculate a first blood flow direction based on a structure of a region of interest rendered in the medical image;
calculate a second blood flow direction based on a structure in a surrounding of the region of interest;
determine an angle formed between the first blood flow direction and the second blood flow direction; and
identify that the larger the determined angle is, the larger an impact is imposed on a human body by the structure of the region of interest or the structure in a surrounding of the region of interest.

13. A medical image processing method, comprising:
obtaining a medical image;
calculating a first blood flow direction based on a structure of a region of interest rendered in the medical image;
calculating a second blood flow direction based on a structure in a surrounding of the region of interest;
determining an angle formed between the first blood flow direction and the second blood flow direction; and
identifying that the larger the determined angle is, the larger an impact is imposed on a human body by the structure of the region of interest or the structure in a surrounding of the region of interest.

14. A storage medium storing therein, in a non-transitory manner, a program that causes a computer to execute processes of:
obtaining a medical image;
calculating a first blood flow direction based on a structure of a region of interest rendered in the medical image;
calculating a second blood flow direction based on a structure in a surrounding of the region of interest;
determining an angle formed between the first blood flow direction and the second blood flow direction; and
identifying that the larger the determined angle is, the larger an impact is imposed on a human body by the structure of the region of interest or the structure in a surrounding of the region of interest.

* * * * *